United States Patent
Hasegawa et al.

(10) Patent No.: US 6,204,229 B1
(45) Date of Patent: Mar. 20, 2001

(54) COMPOSITION TO BE APPLIED TO HAIR OR SKIN

(75) Inventors: Yoshihiro Hasegawa; Shoji Saito, both of Tokyo; Osamu Yamashita, Wakayama; Yoshiaki Fujikura, Haga-gun, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/380,616

(22) PCT Filed: Mar. 18, 1998

(86) PCT No.: PCT/JP98/01144

§ 371 Date: Sep. 17, 1999

§ 102(e) Date: Sep. 17, 1999

(87) PCT Pub. No.: WO98/41185

PCT Pub. Date: Sep. 24, 1998

(30) Foreign Application Priority Data

| Mar. 18, 1997 | (JP) | 9-064606 |
| Mar. 18, 1997 | (JP) | 9-064607 |
| Mar. 18, 1997 | (JP) | 9-064608 |

(51) Int. Cl.$^7$ ........................................... C11D 3/16
(52) U.S. Cl. ........................ 510/101; 510/119; 510/130

(58) Field of Search .................................... 510/101, 103, 510/119, 130

(56) References Cited

U.S. PATENT DOCUMENTS

| 3,875,307 | * | 4/1975 | Wolt et al. | 426/65 |
| 4,218,347 | * | 8/1980 | Naef et al. | 252/522 R |
| 5,180,710 | * | 1/1993 | Naef et al. | 512/26 |
| 5,520,919 | * | 5/1996 | Lerner | 424/401 |
| 5,874,073 | * | 2/1999 | Kaiser et al. | 424/70.11 |

FOREIGN PATENT DOCUMENTS

| 2723312 | * | 2/1996 | (FR) . |
| 63-203609 | * | 8/1988 | (JP) . |
| 64-52711 | * | 2/1989 | (JP) . |
| 8-231354 | * | 9/1996 | (JP) . |

* cited by examiner

*Primary Examiner*—John Hardee
(74) *Attorney, Agent, or Firm*—Oblon, Spivak, McClelland, Maier & Neustadt, P.C.

(57) ABSTRACT

The present invention relates to a composition to be applied to hair or skin, which comprises (A) a surfactant and 0.00025 to 1 wt. % of (B) a perfume substance having an aromatic, pyran or furan ring and a carbonyl group, ether bond, carboxyl group or nonaromatic unsaturated bond, and having a CLogP value not greater than 1.5. The composition has a high perfume retentivity.

18 Claims, No Drawings

COMPOSITION TO BE APPLIED TO HAIR OR SKIN

TECHNICAL FIELD

The present invention relates to a composition exhibiting high perfume retentivity, which is to be applied to hair or skin.

BACKGROUND ART

In order to heighten perfume retentivity, on hair or skin, of a surfactant-containing composition such as detergent, rinse or hair dye after treatment therewith, it is necessary that the perfume remains on the hair or skin treated, the remaining perfume is exhaled and the exhaled perfume is impressive and strong.

It is conventionally known from experience that a perfume substance having a large molecular weight and a low volatility tends to remain on the treated site. For example, in WO96/12876, described is a process for obtaining a perfume composition having high perfume retentivity, which comprises selecting, from perfume substances, low-volatile ones having a boiling point of 250° C. or greater, selecting therefrom a hydrophobic one having a CLogP value of 3 or greater and incorporating such a perfume substance in the perfume composition in an amount of 70% or greater.

DISCLOSURE OF THE INVENTION

Judging from that a perfume is used in various scenes, however, the present inventors considered it necessary to study whether the above-described rule of thumb is applicable to any case. As a result of an extensive investigation on the relation between the site to which a perfume is applied and properties of the perfume exhibited at the site, without being prejudiced by the conventional thought, the present inventors have found a clue of the present invention.

Described specifically, with the foregoing in view, the present inventors investigated on the site to which a perfume substance is applied and the behavior of the substance at the site. It has been found unexpectedly that the above-described rule of thumb is not always applicable to the case where the perfume substance is applied to hair or skin composed of keratin, one of organism-forming components. The detergent system of a shampoo or the like used for hair or skin is usually composed mainly of water and in this system, a perfume substance having a low CLogP value is considered to be washed away together with a large amount of water after use. Finding, among perfume substances having a low CLogP value, the substance exhibiting high perfume retentivity, the present inventors tried to elucidate the reason for it and reached a novel finding that a substance having a specific chemical structure exhibits markedly strong perfume retentivity. As a result of further investigation, it has been found that a perfume substance having a specific chemical structure and has a CLogP value not greater than 1.5 has high perfume retentivity and by using it, a composition having high perfume retentivity to be applied to hair or skin is available, leading to the completion of the present invention.

In the present invention, there is thus provided a composition to be applied to hair or skin, which comprises (A) a surfactant and (B) a perfume substance having an aromatic, pyran or furan ring and a carbonyl group, ether bond, carboxyl group or nonaromatic unsaturated bond, wherein the perfume substance (B) has a CLogP value not greater than 1.5 and is present in an amount from 0.00025 to 1% by weight of the composition.

THE BEST MODE FOR CARRYING OUT THE INVENTION

The perfume substance (B) to be used in the present invention is required to have an aromatic ring, a pyran ring or a furan ring and at least one selected from a carbonyl group, an ether bond, a carboxyl group and a nonaromatic unsaturated bond.

The term "perfume substance" as used herein means an odorant used as a perfume for imparting a pleasant scent.

The perfume substance should have a CLogP value not greater than 1.5, preferably, within a range of from −1.5 to 1.5. At the CLogP value exceeding 1.5, perfume retentivity cannot always be enhanced.

The term "CLogP value" as used herein means a 1-octanol/water partition constant (Log Pow) of a chemical substance and is a value determined by calculation based on the f value method (hydrophobic fragment constant method). The value of CLogP can therefore easily be determined by calculation based on the chemical structure of a perfume substance. Described specifically, it can be determined by decomposing the perfume substance to fragments and integrating the hydrophobic fragment constants (f values) of them.

Among the perfume substances (B) to be used in the present invention, specific examples of the aromatic-ring-containing one include vanillin, cinnamic alcohol, heliotropin, coumarin, 2-methyl-3-(3,4-methylenedioxyphenyl)-propanal, 4-(4-hydroxyphenyl)-2-butanone, benzaldehyde, anise alcohol, 3,4-dimethoxybenzaldehyde, heliotropyl acetate, phenylacetaldehyde dimethyl acetal, phenylacetaldehyde glyceryl acetal, phenylacetic acid and phenoxyethyl alcohol.

Among the perfume substances (B), specific examples of the pyran-ring-containing one include maltol (3-hydroxy-2-methyl-4H-pyran-4-one) and ethylmaltol (2-ethyl-3-hydroxy-4H-pyran-4-one).

Among the perfume substances (B), specific examples of the furan-ring-containing one include sugar lactone (4,5-dimethyl-3-hydroxy-5H-furan-2-one) and furaneol (2,5-dimethyl-4-hydroxy-2H-furan-3-one).

The above-exemplified perfume substances have so far been employed but a composition which permits drastic heightening of their perfume retentivity is utterly unknown. They have been used only for general purposes. Their use for general purposes are described in guiding books of perfume such as "The Chemistry of Perfume" (ed. by The Chemical Society of Japan, written by Ryoichi Akaboshi, published by Dainippon-Tosho Publishing Co., Ltd.), "The Practice of Modern Perfumery" (translated and revised edition, A. J. KRAJKEMAN Dipl. Ing Chem., A.R.I.C. published by INTERSCIENCE PUBLISHER., INC. New York), "Flower oils and Floral Compounds in Perfumery" (written by Danute Pajaujis Anonis, published by Perfumer & Flavorist Allured Publishing Corp. Carol Stream, Ill.), "Perfume and Flavor Chemicals" (written by Steffen Arctander), "Poucher's Perfumes. Cosmetics and Soap" (Ninth edition, written by W. A. Poucher, published by Chapman & Hall), "Perfumery technology" (Wells & Billot published by Artscience Industry) and the like. An example of adding the perfume substance, which is used in the present invention, for the purpose of heightening perfume retentivity, however, cannot be found anywhere in the above-described literatures. For the first time in the present invention, the present inventors have found a process for heightening perfume retentivity of a surfactant composition to be applied to hair or skin by using the above-described perfume substance.

To be more concrete, such perfume substances may be used either singly or in combination and are added in an amount of 0.00025 to 1 wt. %, preferably 0.0005 to 1 wt. % based on the total weight of the composition. Amounts less than 0.00025 wt. % cannot sufficiently heighten the perfume retentivity, while amounts exceeding 1 wt. % impair the storage stability of the composition.

When the perfume substance (B) is a compound having an aromatic ring and a carbonyl group, ether bond, carboxyl group or nonaromatic unsaturated bond, it is added in an amount of 0.25 to 1 wt. %, with 0.5 to 1 wt. % being particularly preferred.

When the perfume substance (B) is a compound having a pyran ring and a carbonyl group, ether bond, carboxyl group or nonaromatic unsaturated bond, it is added in an amount of 0.0025 to 1 wt. %, with 0.005 to 1 wt. % being particularly preferred.

When the perfume substance (B) is a compound having a furan ring and a carbonyl group, ether bond, carboxyl group or nonaromatic unsaturated bond, it is added in an amount of 0.00025 to 1 wt. %, with 0.0005 to 1 wt. % being particularly preferred.

In the present invention, it is possible to add a perfume other than the above-described ones within an extent not impairing the advantages of the present invention. Either of a synthetic perfume or natural perfume may be employed. It can be added singly or as a mixed perfume of at least two kinds.

The composition according to the present invention contains one or more surfactants according to the using purpose.

When the composition is used as a detergent composition for hair or skin, one or more surfactants are added as active components of the detergent composition. Examples of such a surfactant include anionic surfactants, nonionic surfactants and amphoteric surfactants.

Although there is no particular limitation imposed on the anionic surfactant, sulfuric acid type surfactants and sulfonic acid type surfactants, for example, are included.

Examples of the sulfonic or sulfuric acid type anionic surfactant include sulfosuccinic acid base, isethionate base, taurate base, alkylbenzenesulfonic acid base, olefinsulfonic acid base, alkanesulfonic acid base, alkyl or alkenylsulfuric acid base surfactants.

Examples of the sulfosuccinic acid base surfactant include sulfosuccinates of a higher alcohol or ethoxylate thereof and sulfosuccinates derived from a higher fatty acid amide, each represented by the below-described formula (1) or (2) and salts thereof:

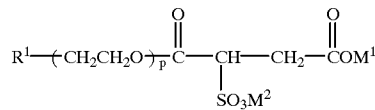

(1)

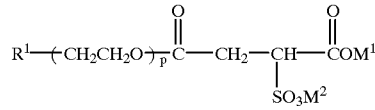

(2)

[wherein $R^1$ represents $R^2$—O— or $R^3$—CO—NH— (in which $R^2$ represents a linear or branched $C_{8-22}$ alkyl or alkenyl group, and $R^3$ represents a linear or branched $C_{7-21}$ alkyl or alkenyl group), $M^1$ and $M^2$ each independently represents a hydrogen atom or a water-soluble-salt-forming cation selected from alkali metals, alkaline earth metals, ammonium and organic ammonium, and p stands for 0 to 20).

Among the compounds represented by the above-described formula (1) and (2), examples of the sulfosuccinate of a higher alcohol or ethoxylate thereof include disodium salts of a sulfosuccinate of a secondary $C_{11-13}$ alcohol ethoxylate ["Softanol MES 3, 5, 7, 9, 12, etc." (these numerals each means the number of the average moles of the added ethylene oxide (EO)), trade name; product of Nippon Shokubai Co., Ltd.], disodium salts ("Kohakule L-400", etc., trade name; product of Toho Chemical Industry, Ltd.) of a sulfosuccinate of lauryl alcohol or lauryl alcohol ethoxylate (EO=3, 4, 6, 9, 12), disodium salts of a sulfosuccinic acid of a synthesized $C_{12-15}$ primary alcohol or ethoxylate thereof (EO=2 to 12) and disodium salts of a sulfosuccinate of a $C_{8-22}$ Guerbet alcohol or ethoxylate (EO=2 to 12) thereof. Examples of the sulfosuccinate derived from a higher fatty acid amide include disodium salts of a sulfosuccinate of lauryl polyethylene glycol (EO=1, 2) amide, disodium salts of a sulfosuccinate of oleyl polyethylene glycol (EO=1, 2) amide and disodium salts of a sulfosuccinate of coconut-oil fatty acid polyethylene glycol (EO=4). Among them, sulfosuccinates of a linear $C_{11-23}$ higher alcohol or ethoxylate thereof, and salts thereof are preferred for good touch feeling and foamability.

Examples of $M_1$ and $M_2$ include sodium, potassium, ammonium, alkanolamines and basic amino acids. In the aforementioned sulfosuccinic acid base surfactant to be used in the present invention, one or more substances as exemplified above are employed optionally as each of $R^1$ portion, $M_1$ portion and $M_2$ portion.

As examples of the isethionate base surfactant, compounds each represented by the following formula (3):

$$R^4COOCH_2CH_2SO_3M^3 \quad (3)$$

(wherein, $R^4$ represents an alkyl, alkenyl or hydroxyalkyl group having 7 to 19 carbon atoms on average, and $M^3$ represents an alkali metal or organic amine) can be mentioned.

In the above-described formula (3), examples of the fatty acid residue $R^4COO$— include $C_{11}H_{23}COO$—, $C_{13}H_{27}COO$—, $C_{15}H_{31}COO$—, $C_{17}H_{35}COO$— and coconut-oil fatty acid residue, while those of the counterion $M^3$ include lithium, potassium, sodium, monoethanolamine, diethanolamine and triethanolamine.

Examples of the taurate base surfactant include compounds each represented by the following formula (4):

(4)

(wherein, $R^5$ represents an alkyl, alkenyl or hydroxyalkyl group having 7 to 19 carbon atoms on average, $R^6$ represents a lower alkyl or hydroxyalkyl group having 1 to 3 carbon atoms on average and $M^4$ represents an alkali metal or organic amine).

In the above-described formula (4), examples of the alkyloyl group $R^5CO$— include a lauroyl group, a palmitoyl group, a stearoyl group, an oleoyl group and a cocoyl group derived from coconut-oil fatty acid (alkyloyl groups having as $R^5$ a group having carbon atoms ranging from 7 to 19), while those of the alkyl group $R^6$ include methyl, ethyl and propyl groups. Examples of the counterion $M^4$ include lithium, potassium, sodium, triethanolamine, diethanolamine and monoethanolamine.

As examples of the olefinsulfonic acid base surfactant, olefinsulfonates having, in one molecule thereof, 10 to 20 carbon atoms on average can be mentioned, while as examples of the alkanesulfonic acid type surfactant, alkanesulfonates having, in one molecule thereof, 10 to 20 carbon atoms on average can be mentioned. Examples of the alkyl- or alkenylsulfuric acid base surfactant include alkyl or alkenyl ether sulfates each having a linear or branched alkyl or alkenyl group having 10 to 20 carbon atoms on average, and having, in one molecule thereof, 0.5 to 8 moles on average of ethylene oxide and propylene oxide added at a ratio of 0.1/9.9 to 9.9/0.1 or ethylene oxide and butylene oxide added at a ratio of 0.1/9.9 to 9.9/0.1; and alkyl- or alkenylsulfates containing an alkyl or alkenyl group having 10 to 20 carbon atoms on average.

Examples of the nonionic surfactant include fatty acid amides, polyoxyethylene alkyl ethers, sugar esters, sugar ethers and sugar amides.

Exemplary amphoteric surfactants include imidazoline and betaine base surfactants.

Although no particular limitation is imposed on the amount of the surfactant, it is preferably added in an amount of 5 to 50 wt. % based on the total weight of the detergent composition, with 5 to 30 wt. % being particularly preferred.

When the composition of the present invention is used as a rinse composition, a cationic surfactant is added as a rinse component. Examples of such a cationic surfactant include compounds represented by the following formula (5), (6) or (7):

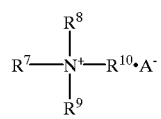

(5)

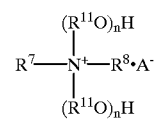

(6)

(wherein, $R^7$ represents a linear or branched $C_{8-22}$ alkyl or alkenyl group, $R^8$ represents a hydrogen atom, a methyl group, an ethyl group or a linear or branched $C_{8-22}$ alkyl or alkenyl group, $R^9$ and $R^{10}$ each independently represents a hydrogen atom, a methyl group or an ethyl group, $R^{11}$ represents a $C_{2-3}$ alkenylene group, A represents a halogen atom or an organic anion group and n stands for 1 to 10),

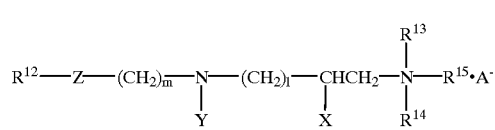

(7)

(wherein, $R^{12}$ represents a linear or branched $C_{7-35}$ alkyl or alkenyl group, $R^{13}$, $R^{14}$ and $R^{15}$ are the same or different and each independently represents a $C_{1-4}$ alkyl or hydroxyalkyl group or a hydrogen atom, Z represents —CONJ (in which J means a hydrogen atom or a $C_{1-3}$ alkyl or hydroxyalkyl group), —O— or —COO—, Y represents a hydrogen atom, a hydroxyl group, a linear or branched $C_{1-36}$ alkyl, alkenyl or hydroxyalkyl group or a group represented by the following formula:

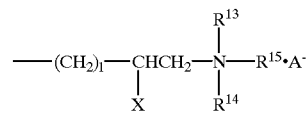

X represents a hydrogen atom or a hydroxyl group, m stands for 2 or 3, l stands for 0 or an integer of 1 to 5, with the proviso that when l=1, X represents a hydrogen atom or a hydroxyl group and when l=0, 2, 3, 4 or 5, X represents a hydrogen atom, and A has the same meaning as described above).

Among the above-described cationic surfactants, lauryl trimethylammonium chloride, stearyl trimethylammonium chloride, cetyl trimethylammonium chloride and distearyl dimethylammonium chloride are particularly preferred.

Although no particular limitation is imposed on the amount of the cationic surfactant, it is preferably added in an amount of 0.5 to 25 wt. % based on the total weight of the rinse composition, with 2 to 10 wt. % being particularly preferred.

When the composition of the present invention is employed as a hair dye composition, an anionic surfactant, nonionic surfactant or amphoteric surfactant similar to the above-exemplified one is added to dissolve the composition in the surfactant. Although no particular limitation is imposed on the amount of such a surfactant, it is preferably added in an amount of 5 to 50 wt. % based on the total weight of the hair dye composition, with 5 to 30 wt. % being particularly preferred.

Moreover, it is possible to add, to the composition of the present invention, a component ordinarily used for detergents, rinses, hair dyes and the like, as another additive. Examples include humectants such as propylene glycol, sorbitol and glycerin, viscosity regulators such as carboxyvinyl polymer, methyl cellulose, ethanol and polyoxyethylene glycol distearate, pearlizing agent, pigment, ultraviolet absorber, antioxidant, sterilizer, anti-inflammatory and antiseptic. Such an additive can be used as needed within an extent not impairing the advantages of the present invention.

The composition of the present invention can be prepared in a conventional manner and it can be formulated as, for example, a liquid, paste, gel or solid.

The composition of the present invention can be applied to any product insofar as it requires perfume retentivity on hair or skin. It is used for hair detergents such as shampoo and rinse-in shampoo, skin detergents such as body shampoo and face wash and rinse compositions such as hair rinsing and hair conditioner. In addition, it is suited for products, such as hair dye composition, which must be washed away after used.

EXAMPLES

The present invention will hereinafter be described more specifically by reference of examples. It should however be borne in mind that the present invention is not limited to these examples.

Example 1

A hair detergent composition composed of the following ingredients was used to prepare a test composition containing each perfume substance which varies with the Example numbers shown by Tables 1 to 3. Thus prepared compositions were subjected to an evaluation test of perfume retentivity. Results are shown in Tables 1 to 3.

| Hair detergent | |
|---|---|
| (Ingredients) | (wt. %) |
| Sodium polyoxyethylene (EO = 3) lauryl ether sulfate solution | 16 |
| Lauryl diethanolamide | 2 |
| Sodium benzoate | 0.55 |
| Dibutylhydroxytoluene | 0.1 |
| Water | balance |

(Evaluation Method)

A bundle (20 g) of homogeneous human hair was immersed in warm water of 36° C. and wetted sufficiently with water. The bundle was then shampooed with 3 g of each test composition for 3 minutes. After washing with warm water of 36° C., the bundle was dried. The remaining perfume of the human hair bundle after treatment was evaluated by a panel of experts in accordance with the following standards.

⊚: Strong perfume retentivity was recognized well from rightly after the treatment.

○: Strong perfume retentivity was recognized from rightly after the treatment.

X: Strong perfume retentivity was not recognized from rightly after the treatment.

TABLE 1

| Exec. No. | Perfume substance | CLogP | Amount added (wt. %) | | |
|---|---|---|---|---|---|
| | | | 0.025 | 0.25 | 0.50 |
| 1 | Vanillin | 1.354 | x | ○ | ⊚ |
| 2 | Cinnamic alcohol | 1.400 | x | ○ | ⊚ |
| 3 | Heliotropin | 1.257 | x | ○ | ⊚ |
| 4 | Coumarin | 1.412 | x | ○ | ⊚ |
| 5 | 2-Methyl-3-(3,4-methylenedioxy-phenyl)propanal | 1.387 | x | ○ | ⊚ |
| 6 | 4-(4-Hydroxyphenyl)-2-butanone | 1.072 | x | ○ | ⊚ |
| 7 | Benzaldehyde | 1.495 | x | ○ | ⊚ |
| 8 | Anise alcohol | 1.023 | x | ○ | ⊚ |
| 9 | 314-Dimethoxybenzaldehyde | 1.350 | x | ○ | ⊚ |
| 10 | Heliotropyl acetate | 1.315 | x | ○ | ⊚ |
| 11 | Phenylacetaldehyde dimethyl acetal | 1.293 | x | ○ | ⊚ |
| 12 | Pheoxyethyl alcohol | 1.188 | x | ○ | ⊚ |
| 13 | Phenylacetaldehyde glyceryl acetal | 0.833 | x | ○ | ⊚ |
| 14 | Linalool | 2.549 | x | x | x |
| 15 | Camphor | 2.177 | x | x | x |
| 16 | Terpineol | 2.629 | x | x | x |
| 17 | Citronellol | 3.253 | x | x | x |
| 18 | Geraniol | 2.769 | x | x | x |
| 19 | Benzyl alcohol | 1.104 | x | x | x |
| 20 | Phenyl ethyl alcohol | 1.183 | x | x | x |

TABLE 2

| Exec. No. | Perfume substance | CLogP | Amount added (wt. %) | | |
|---|---|---|---|---|---|
| | | | 0.0020 | 0.0025 | 0.0050 |
| 21 | Maltol | −0.062 | x | ○ | ⊚ |
| 22 | Ethyl maltol | 0.467 | x | ○ | ⊚ |
| 23 | 3,7-Dimethyl-2,6-oXtadienal | 3.120 | x | x | x |
| 24 | Nonanal | 2.995 | x | x | x |

TABLE 3

| Exec. No. | Perfume substance | CLogP | Amount added (wt. %) | | |
|---|---|---|---|---|---|
| | | | 0.00005 | 0.00025 | 0.00050 |
| 25 | Furaneol | 0.413 | x | ○ | ⊚ |
| 26 | Sugar lactone | 0.888 | x | ○ | ⊚ |
| 27 | 2,6-Nonadienal | 2.851 | x | x | x |
| 28 | Methyloctylcarbonate | 3.097 | x | x | x |

From the results shown in Tables 1 to 3, it has been found that from rightly after treatment with the hair detergent compostion according to the present invention which contained 0.00025 to 1 wt. % of a specific perfume substance, a marked increase in the perfume retentivity was recognized.

Example 2

A rinse composition composed of the following ingredients was used to prepare a test composition containing each perfume substance which varies with the Example numbers shown by Tables 4 to 6. Thus prepared compositions were subjected to an evaluation test of perfume retentivity. Results are shown in Tables 4 to 6.

| Rinse composition | |
|---|---|
| (Ingredients) | (wt. %) |
| Stearyl trimethylammonium chloride | 3.6 |
| Cetanol | 3.5 |
| Paraoxybenzoate ester | 0.1 |
| Water | balance |

(Evaluation Method)

A bundle (20 g) of heterogeneous human hair was immersed in warm water of 36° C. and wetted sufficiently with water. The bundle was shampooed and then rinsed with 3 g of each test compostion. After washing with warm water of 36° C., the bundle was dried. The remaining perfume of the human hair bundle after treatment was evaluated by a panel of experts in accordance with the below-described standards.

TABLE 4

| Exec. No. | Perfume substance | CLogP | Amount added (wt. %) | | |
|---|---|---|---|---|---|
| | | | 0.025 | 0.25 | 0.50 |
| 1 | Vanillin | 1.354 | x | ○ | ⊚ |
| 2 | Cinnamic alcohol | 1.400 | x | ○ | ⊚ |
| 3 | Heliotropin | 1.257 | x | ○ | ⊚ |
| 4 | Coumarin | 1.412 | x | ○ | ⊚ |
| 5 | 2-Methyl-3-(3,4-methylenedioxy-phenyl)propanal | 1.387 | x | ○ | ⊚ |
| 6 | 4-(4-Hydroxyphenyl)-2-butanone | 1.072 | x | ○ | ⊚ |
| 7 | Benzaldehyde | 1.495 | x | ○ | ⊚ |
| 8 | Anise alcohol | 1.023 | x | ○ | ⊚ |
| 9 | 3,4-Dimethoxybenzaldehyde | 1.350 | x | ○ | ⊚ |
| 10 | Heliotropyl acetate | 1.315 | x | ○ | ⊚ |
| 11 | Phenylacetaldehyde dimethyl acetal | 1.293 | x | ○ | ⊚ |
| 12 | Pheoxyethyl alcohol | 1.188 | x | ○ | ⊚ |
| 13 | Phenylacetaldehyde glyceryl acetal | 0.833 | x | ○ | ⊚ |
| 14 | Linalool | 2.549 | x | x | x |
| 15 | Camphor | 2.177 | x | x | x |
| 16 | Terpineol | 2.629 | x | x | x |
| 17 | Citronellol | 3.253 | x | x | x |

TABLE 4-continued

| Exec. | | | Amount added (wt. %) | | |
|---|---|---|---|---|---|
| No. | Perfume substance | CLogP | 0.025 | 0.25 | 0.50 |
| 18 | Geraniol | 2.769 | x | x | x |
| 19 | Benzyl alcohol | 1.104 | x | x | x |
| 20 | Phenyl ethyl alcohol | 1.183 | x | x | x |

TABLE 5

| Exec. | | | Amount added (wt. %) | | |
|---|---|---|---|---|---|
| No. | Perfume substance | CLogP | 0.0020 | 0.0025 | 0.0050 |
| 21 | Maltol | −0.062 | x | ○ | ⊚ |
| 22 | Ethyl maltol | 0.467 | x | ○ | ⊚ |
| 23 | 3,7-Dimethyl-2,6-octadienal | 3.120 | x | x | x |
| 24 | Nonanal | 2.995 | x | x | x |

TABLE 3

| Exec. | | | Amount added (wt. %) | | |
|---|---|---|---|---|---|
| No. | Perfume substance | CLogP | 0.025 | 0.25 | 0.50 |
| 25 | Furaneol | 0.413 | x | ○ | ⊚ |
| 26 | Sugar lactone | 0.888 | x | ○ | ⊚ |
| 27 | 2,6-Nonadienal | 2.851 | x | x | x |
| 28 | Methyloctylcarbonate | 3.097 | x | x | x |

From the results shown in Tables 4 to 6, it has been found that from rightly after treatment with the rinse according to the present invention which contained 0.00025 to 1 wt. % of a specific perfume substance, a marked increase in the perfume retentivity was recognized.

It should be noted that a skin detergent and a rinse composition prepared and evaluated in a similar manner to Example 1 or 2 also exhibited high perfume retentivity on the skin as a result of evaluation.

Capability of Exploitation in Industry

The composition according to the present invention has heightened perfume retentivity, more specifically, exhibits heightened perfume retentivity rightly after the composition is washed away after cleansing, rinsing or hair dying therewith.

What is claimed is:

1. A composition to be applied to hair or skin, which comprises (A) a surfactant and (B) a perfume substance not including phenoxyethyl alcohol having an aromatic, pyran or furan ring and a carbonyl group, ether bond, carboxyl group or nonaromatic unsaturated bond, wherein the perfume substance (B) has a CLogP value not greater than 1.5 and is present in an amount from 0.25 to 1% by weight of the composition.

2. A composition according to claim 1, wherein the perfume substance (B) is a compound having an aromatic ring and a carbonyl group, ether bond, carboxyl group or nonaromatic unsaturated bond.

3. A composition according to claim 1, wherein the perfume substance (B) is a compound having a pyran ring and a carbonyl group, ether bond, carboxyl group or non-aromatic unsaturated bond.

4. A composition according to claim 1, wherein the perfume substance (B) is a compound having a furan ring and a carbonyl group, ether bond, carboxyl group or non-aromatic unsaturated bond.

5. A composition according to claim 1 or 2, wherein the perfume substance (B) is selected from vanillin, cinnamic alcohol, heliotropin, coumarin, 2-methyl-3-(3,4-methylenedioxy-phenyl)-propanal, 4-(4-hydroxyphenyl)-2-butanone, benzaldehyde, anise alcohol, 3,4-dimethoxybenzaldehyde, heliotropyl acetate, phenylacetaldehyde dimethyl acetal, phenylacetaldehyde glyceryl acetal, and phenylacetic acid.

6. A composition according to claim 1 or 3, wherein the perfume substance (B) is maltol or ethyl maltol.

7. A composition according to claim 1 or 4, wherein the perfume substance (B) is 4,5-dimethyl-3-hydroxy-5H-furan- or furaneol.

8. A composition to be applied to hair or skin according to claim 1, which is a detergent composition, rinse composition, or hair dye composition.

9. A method for enhancing the perfume retentability of a composition to be applied to hair or skin, comprising mixing (A) a surfactant and (B) a perfume substance not including phenoxyethanol, said perfume substance having a CLogP value not greater than 1.5 and being a compound having an aromatic ring and a carbonyl group, ether bond, carboxyl group or non aromatic unsaturated bond and being present in an amount of from 0.25 to 1% by weight of the composition.

10. The method as claimed in claim 9, wherein the perfume substance (B) is selected from the group consisting of vanillin, cinnamic alcohol, heliotropin, coumarin, 2-methyl-3-(3,4-methylenedioxy-phenyl)-propanal, 4-(4-hydroxyphenyl)-2-butanone, benzaldehyde, anise alcohol, 3,4-dimethoxybenzaldehyde, heliotropyl acetate, phenylacetaldehyde dimethyl acetal, phenylacetaldehyde glyceryl acetal and phenylacetic acid.

11. A method for heightening perfume retentivity on hair or skin, comprising applying the composition according to claim 1 to hair or skin.

12. A method for heightening perfume retentivity on hair or skin, comprising applying the composition according to claim 2 to hair or skin.

13. A method for heightening perfume retentivity on hair or skin, comprising applying the composition according to claim 3 to hair or skin.

14. A method for heightening perfume retentivity on hair or skin, comprising applying the composition according to claim 4 to hair or skin.

15. A method for heightening perfume retentivity on hair or skin, comprising applying the composition according to claim 5 to hair or skin.

16. A method for heightening perfume retentivity on hair or skin, comprising applying the composition according to claim 6 to hair or skin.

17. A method for heightening perfume retentivity on hair or skin, comprising applying the composition according to claim 7 to hair or skin.

18. A method for heightening perfume retentivity on hair or skin, comprising applying the composition according to claim 8 to hair or skin.

* * * * *

UNITED STATES PATENT AND TRADEMARK OFFICE
CERTIFICATE OF CORRECTION

PATENT NO. : 6,204,229 B1  
DATED : March 20, 2001  
INVENTOR(S) : Yoshihiro Hasegawa, et al.

It is certified that error appears in the above-identified patent and that said Letters Patent is hereby corrected as shown below:

Column 10,  
Line 18, "or furaneol." should read -- 2-one --.

Signed and Sealed this

Twenty-seventh Day of November, 2001

Attest:

NICHOLAS P. GODICI  
Attesting Officer    Acting Director of the United States Patent and Trademark Office